United States Patent
Giorno

(10) Patent No.: US 7,217,130 B2
(45) Date of Patent: May 15, 2007

(54) PROSTHESIS MOUNTING DEVICE AND ASSEMBLY

(76) Inventor: Thierry Giorno, 18 Avenue Sevigne, Nice (FR) 06100

( * ) Notice: Subject to any disclaimer, the term of this patent is extended or adjusted under 35 U.S.C. 154(b) by 118 days.

(21) Appl. No.: 10/453,309

(22) Filed: Jun. 3, 2003

(65) Prior Publication Data
US 2004/0018471 A1    Jan. 29, 2004

Related U.S. Application Data

(63) Continuation-in-part of application No. 10/165,332, filed on Jun. 7, 2002, now Pat. No. 7,033,174.

(51) Int. Cl.
*A61C 8/00* (2006.01)
(52) U.S. Cl. .................... 433/174
(58) Field of Classification Search ............... 433/173, 433/174
See application file for complete search history.

(56) References Cited

U.S. PATENT DOCUMENTS

| | | | |
|---|---|---|---|
| 2,112,007 A * | 3/1938 | Pinkney ................... 433/174 |
| 3,466,748 A | 9/1969 | Christensen | |
| 3,672,058 A * | 6/1972 | Nikoghossian ............ 433/174 |
| 3,732,621 A * | 5/1973 | Bostrom ................... 433/174 |
| 4,193,194 A | 3/1980 | Dalise | |
| 4,202,101 A | 5/1980 | Weissman | |
| 4,290,755 A * | 9/1981 | Scott ....................... 433/173 |
| 4,728,292 A | 3/1988 | Lustig et al. | |
| 4,767,332 A | 8/1988 | Weissman | |
| 4,793,808 A * | 12/1988 | Kirsch ...................... 433/173 |
| 4,826,434 A | 5/1989 | Krueger | |
| 5,049,072 A * | 9/1991 | Lueschen ................. 433/173 |
| 5,087,200 A * | 2/1992 | Brajnovic et al. ......... 433/173 |
| 5,205,745 A | 4/1993 | Kamiya et al. | |
| 5,209,666 A * | 5/1993 | Balfour et al. ............ 433/173 |
| 5,211,561 A * | 5/1993 | Graub ...................... 433/169 |
| 5,263,996 A | 11/1993 | Filhol | |
| 5,312,255 A | 5/1994 | Bauer | |
| 5,376,004 A * | 12/1994 | Mena ....................... 433/173 |
| 5,520,540 A | 5/1996 | Nardi et al. | |
| 5,639,237 A | 6/1997 | Fontenot | |
| 5,662,475 A | 9/1997 | Mena | |

(Continued)

OTHER PUBLICATIONS

IMTEC Sendax Mini Dental Implant System (MDI), Small Wonder, 4-page color brochure.

(Continued)

*Primary Examiner*—Ralph A. Lewis
(74) *Attorney, Agent, or Firm*—Reising, Ethington, Barnes, Kisselle, P.C.

(57) ABSTRACT

A prosthesis mounting device and assembly for securing a prosthesis on an implant supported in bone tissue. A metallic appendage or "preppable abutment" is carried by a dental implant and is milled or "prepped" into a shape suitable to accept a dental prosthetic. A recess extends axially upwardly from an axial bottom end of the appendage and is shaped to fit over an O-ring receiver abutment or "O-ball" of a dental implant.

17 Claims, 7 Drawing Sheets

U.S. PATENT DOCUMENTS 5,685,714 A * 11/1997 Beaty et al. ................. 433/172
5,704,788 A * 1/1998 Milne .......................... 433/173
5,733,124 A * 3/1998 Kwan .......................... 433/173
5,749,732 A 5/1998 Sendax
5,882,200 A * 3/1999 Sutter et al. ................ 433/173
5,967,783 A 10/1999 Ura
6,655,962 B1 * 12/2003 Kennard ..................... 433/174
6,716,030 B1 * 4/2004 Bulard et al. ............... 433/174

OTHER PUBLICATIONS

Dental Attachment Systems, The AIT Attachment for Retained Natural Tooth Roots, pp. 6 and 7.

Core-Vent Implant System, Core-Vent Corporation, 6 pages from catalog.

IMTEC Sendax MDI System, 5 pages of Product Description.

* cited by examiner

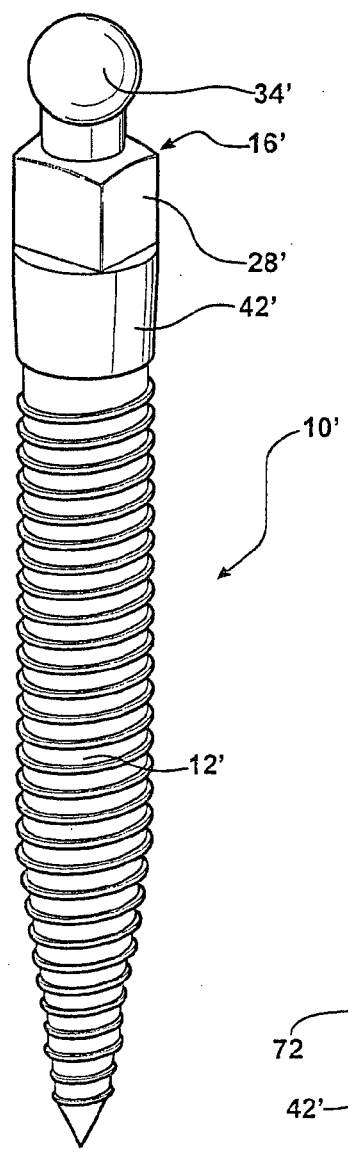
FIG - 8
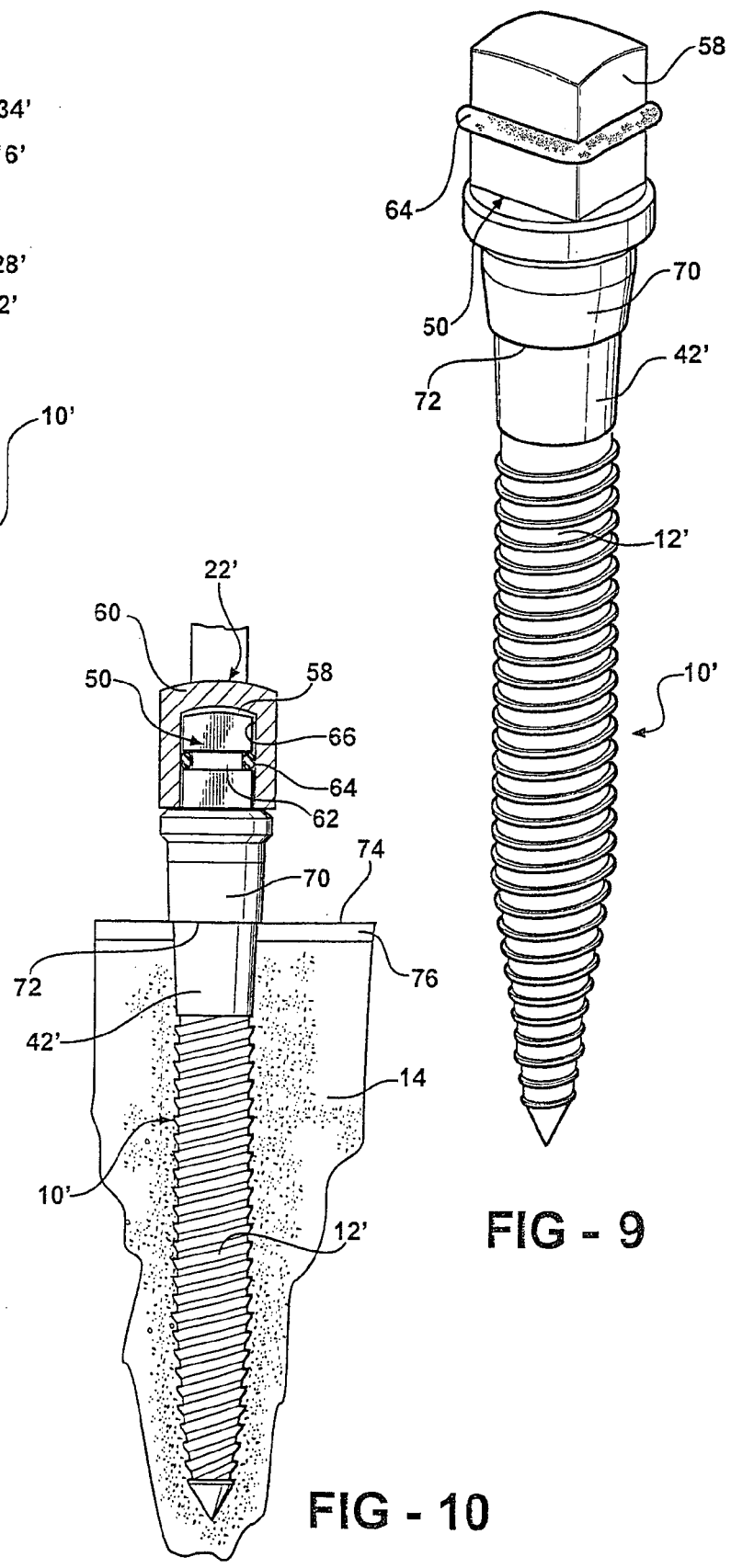
FIG - 9
FIG - 10

PROSTHESIS MOUNTING DEVICE AND ASSEMBLY

CROSS-REFERENCES TO RELATED APPLICATIONS

This application is a continuation-in-part of application Ser. No. 10/165,332, filed Jun. 7, 2002, now U.S. Pat. No. 7,033,174.

STATEMENT REGARDING FEDERALLY SPONSORED RESEARCH OR DEVELOPMENT

Not Applicable

BACKGROUND OF THE INVENTION

1. Field of the Invention

This invention relates generally to a prosthesis mounting device for securing a prosthesis on an implant supported in bone tissue.

2. Description of the Related Art Including Information Disclosed Under 37 CFR 1.97 and 1.98

Conventional crowns, bridges and dentures have long been the standard prosthetic devices used to replace missing teeth. Such devices are secured to a jaw bone using a surgical anchor known as a dental implant or a prosthesis mounting device.

The design of dental implants has developed considerably over the years since their initial conception by the ancient Egyptians. One of the more important developments is credited to the Swedish firm, Noblepharma. In the mid-1980s, Noblepharma developed and marketed a dental implant that resembled a natural tooth root. This implant, known as a root form implant, include two major components: a bone screw and a prosthetic abutment interface. There are now about 10 major dental implant manufacturers in the United States alone that market various forms of the root form implant.

The protocol for surgical placement of a root form implant is to first expose an underlying jaw bone through a surgical intervention of the soft tissue covering the jaw bone. An opening is then created in the jaw bone equal to the minor diameter of the bone screw portion of the implant. This is done by using a series of expanding diameter surgical drills that allow the surgeon to gradually increase the size of the hole in the bone until the implant can be screwed into place. Once the implant has been screwed in, the soft tissue incision is sutured closed over the osteotomy site. In a process known in the art as osseointegration, the bone tissue around the device then grows into tight apposition to the screw during a three to six month healing process.

In recent years, however, some doctors have advocated what is known in the art as immediate or progressive loading of an implant. This process eliminates or shortens the time required for osseointegration and its associated long healing times. However, most implants still require that patients wait for an extended time before they can fully make use of permanent replacement teeth. Multiple surgeries are also required.

After a root form screw implant is firmly positioned in bone, and once the osseointegration process is complete, the tissue covering the osteotomy site is again reflected and an attachment device called an abutment is affixed to a head of the implant that remains exposed after installation. A dental prosthetic can then be cemented or screwed onto the prosthetic abutment portion of the implant. The prosthetic abutment portion of the device is available in many shapes, sizes and designs to accommodate various treatment applications.

Extending healing periods and costs associated with the above described two-stage surgical implant procedure have prevented traditional dental implant systems from becoming the chosen treatment modality for patients with missing teeth. Manufacturers and marketers of dental implants have been searching for new concepts and ideas that would provide a more economical and less surgically invasive system.

In response to this need, a New York City company called Dentatus® USA Ltd. began experimenting with endodontic posts designed to be implanted directly into a jaw bone. These endontic posts, known as MTI implants, had a one-piece design incorporating both screw and abutment. Because the diameter of the MTI implant was only 1.8 mm, Dentatus® was able to develop an implantation procedure that did not require a large opening in the bone to receive the implant. All that was necessary was a small, shallow starter hole that could be formed in jaw bone tissue directly through soft tissue without having to surgically lay back a flap of the soft tissue to expose the bone beneath. This new approach was minimally invasive and provided an implant that could be immediately loaded without having to wait for an extended period of time for osseointegration to occur. In the art, this new type of implant that's dimensionally small enough to self-tap into bone tissue without splitting the bone tissue became known as the mini dental implant.

While some standard sized (approx. 3.75 mm diameter) implants claim to be self-tapping, because of their larger size, the extent of their self-tapping is severely limited. Bone has a visco-elastic nature that allows it stretch, to a certain point, to accommodate inserted objects. However, to install an implant shaft larger than approximately 2.0 mm in diameter requires a large osteotomy formed by drilling progressively larger osteotomy holes to the full depth that the implant will extend into the bone. For example, a so-called self-tapping implant having a 3.75 mm diameter and 4.0 mm diameter threads will still require a 3.0 mm osteotomy. A cutter is supported near the tip of such an implant and extends radially outward to engage and form thread grooves in the wall of a 3.75 mm osteotomy as the implant is installed.

IMTEC® Corporation is currently marketing a Sendax mini dental implant system that comprises a prosthesis mounting device having a threaded shaft, and an abutment including a square nut and a ball-shaped O-ring abutment. The threaded shaft is tapered at a first end to allow the shaft to self-tap into bone tissue starting from a small, shallow pilot hole formed in bone tissue. Because the shaft self-taps past the depth of the pilot hole, it immediately integrates with the bone tissue. The square nut is attached to and extends integrally and axially from a second end of the threaded shaft opposite the first end. The O-ring abutment is attached to and extends integrally and axially from the square abutment. The O-ring abutment is shaped to engage and support a prosthetic tooth or set of teeth. However, this system is unable to disconnect or automatically discontinue torque application during installation when a predetermined bone density is encountered. Nor can such a device warn an installer that the bone tissue lacks sufficient density to properly support a prosthetic tooth. Still further, the Sendax mounting system cannot indicate to an installer when it is fully seated in bone tissue, the platform formed at the head area of the shaft is no greater than the cross-sectional area of the shaft itself and provides little support for a prosthesis, and it doesn't provide a satisfactory interface between the implant and surrounding soft tissues.

In implant dentistry, it is also known for a prosthesis mounting assembly to include a large titanium appendage or "preppable" abutment that detachably extends from an axial top surface of a full-sized dental implant or "tooth post". Such a preppable abutment is milled or "prepped", as a tooth would be prepped, into a generally triangular prism-like shape suitable to accept and support a crown or bridge. It's then fixed to the top surface of an implant using an axially-oriented prosthetic fixation screw. Typically, a preppable abutment of this type will also include either an internal or an external hex key or recess that engages a complementary recess or key formed on or in the axial top surface of an implant and the appendage may be milled either in the mouth of a model using a dentist's drill or by sending the preppable abutment to dental lab where a milling machine is used to prep the appendage.

In practice, an implant is first surgically installed by incising and laying back gum tissue to reveal jaw bone tissue, drilling a hole in the bone, inserting the implant, then closing the gum tissue over the osteotomy site and allowing oseointegration to occur. The preppable abutment is then installed on the implant by re-incising and laying back the gum tissue to reveal the axial top surface of the implant, positioning the preppable abutment on the implant, and fixing it in place with the prosthetic fixation screw. The gum tissue is then closed and allowed to heal. An impression is then taken of the preppable abutment and a coping is formed in the impression to duplicate the preppable abutment. The coping is used to form a stone model duplicating the patient's mouth. A prosthetic tooth or bridge is then formed on the stone model and coping to fit in the patient's mouth and over the preppable abutment extending upward from the embedded implant. Finally, the prosthetic tooth or bridge is supported on the preppable abutment. However, this type of preppable abutment requires an implant that is specifically configured to accept and support it. IN addition, this design is prone to micro movement that can but stress on and eventually break a prosthetic tooth or bridge.

What's needed is a prosthesis mounting device and assembly that doesn't require an implant that's specifically designed to support it.

BRIEF SUMMARY OF THE INVENTION

According to the invention, a prosthesis mounting device is provided for securing a prosthesis on an implant supported in bone tissue. The device includes a metallic appendage that's configured to be carried by a dental implant, and to be milled into a shape suitable to accept a dental prosthetic. The device also includes a recess that extends axially upwardly from an axial bottom end of the appendage and is configured to fit over an O-ring receiver abutment of a dental implant.

Because the device fits over an O-ring receiver abutment, it allows for the manufacture of a single implant that can be used to support either a preppable abutment or a prosthetic having an O-ring interface. It also obviates the need for a surgical operation to install the preppable abutment on an implant after the implant has been installed. Also, a preppable abutment constructed according to the invention is able to function as an impression coping since it can come off in an impression tray. Still further, it can be secured in place on an implant without requiring a fixation screw.

According to another aspect of the invention, a prosthesis mounting assembly is provided for securing a prosthesis on an implant supported in bone tissue. The assembly comprises an implant having a threaded shaft configured to be screwed into bone tissue and an O-ring receiver abutment attached to and axially extending from an aft end of the shaft. The assembly also includes a preppable abutment that fits over and is supported on the O-ring receiver abutment of the implant.

The invention also includes a method for securing a prosthesis on a patient's jaw bone in the patient's oral cavity. According to this method, one or more implants are installed in a patient's jaw bone, each implant including an O-ring receiver abutment. A preppable abutment is then removably received on the or each implant. The or each preppable abutment is then prepped, and one or more dental prosthetics are formed to be supported on the or each preppable abutment. The or each preppable abutment is supported on the or each implant.

BRIEF DESCRIPTION OF THE SEVERAL VIEWS OF THE DRAWINGS

These and other features and advantages of the invention will become apparent to those skilled in the art in connection with the following detailed description and drawings, in which:

FIG. 8 is a front isometric view of a prosthesis mounting device constructed according to a second embodiment of the invention;

FIG. 9 is an isometric view of a driver adapter supported on the mounting device of FIG. 8;

FIG. 10 is a front view of a ratchet wrench engaging the driver adapter of FIG. 9 and showing a threaded portion of the mounting device disposed in bone tissue;

DETAILED DESCRIPTION OF INVENTION EMBODIMENT(S)

Figure 1:
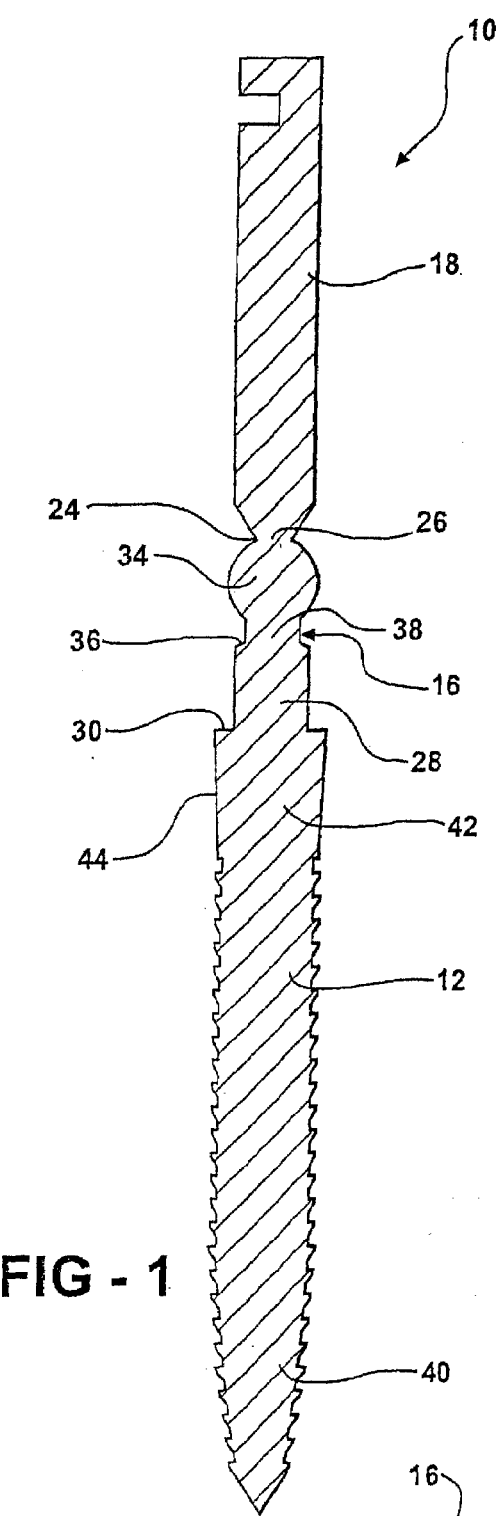
FIG. 1 is a front view of a prosthesis mounting device constructed according to a first embodiment of the invention.

A first embodiment of a prosthesis mounting device for securing a prosthesis such as a prosthetic tooth on bone tissue 14 is generally shown at 10 in FIGS. 1–7. A second embodiment is shown at 10' in FIGS. 9 and 10. Reference numerals with the designation prime (') in FIGS. 9 and 10, and in FIGS. 8 and 11–14, indicate alternative configurations of elements that also appear in the first embodiment. Unless indicated otherwise, where a portion of the following description uses a reference numeral to refer to the figures, that portion of the description is intended to apply equally to elements designated by primed numerals in FIGS. 8–14.

The driver adapter recess 52 is defined by a socket 70 having a leading rim 72 positioned to contact an upper surface 74 of a gingival tissue layer 76 when the threaded shaft portion 12' of the prosthetic mounting device 10' has been driven to a proper depth into bone tissue 14 beneath the gingival tissue layer 76, i.e., a depth at which the abutment 16' is supported in a position such that a prosthesis mounted on the abutment 16' will abut the upper surface 74 of the gingival tissue layer 76 as shown in FIG. 10.

The leading rim 72 of the driver adapter socket 70 is also positioned to contact the upper surface 74 of the gingival tissue layer 76 when the threaded shaft portion 12' of the prosthetic mounting device 10' has been driven to a depth into bone 14 that leaves an upper portion of the collar 42' protruding from an upper surface 80 of the bone 14. In this position, and as best shown in FIG. 10, the protruding upper portion of the collar 42' laterally abuts a surrounding portion of a gingival tissue layer overlying the bone.

To accurately secure a prosthesis in bone tissue to a proper or desired depth, the driver adapter 50 is connected to the mounting device 10' such that the axially inner chamber 54 of the recess 52 engages and axially retains the 0-ring abutment 34' and an axially outer portion 56 of the recess 52 rotatably engages the nut 28'. A rotary driver 22' is then connected to the driver adapter 50. The mounting device 10' is then screwed into bone tissue 14 by engaging the threaded shaft 12' in the bone tissue 14 and operating the rotary driver 22' to rotate the driver adapter 50 and mounting device 10'. Proper mounting device depth is determined as being the depth of the mounting device 10' when the leading rim 72 of the driver adapter socket 70 contacts the upper surface 74 of the gingival tissue layer 76 as shown in FIG. 10.

The device 10 includes a threaded shaft 12 or bone screw that is screwed into bone tissue 14 and a prosthetic abutment 16 attached to and axially extending from an aft end of the shaft 12. The abutment 16 engages and supports a prosthesis to serve as an interface between the prosthesis mounting device 10 and a prosthesis. The device 10 also includes an installation handle 18 connected to and extending axially from the abutment 16. The handle 18 is engaged and rotated by a manual or motor driven rotary driver 20 and is detached from the abutment 16 under a pre-determined torque load so that the handle 18 breaks off when bone tissue of a predetermined density is encountered. This prevents an installer from continuing to use the rotary driver 20 when bone density requires that a different instrument, such as a ratchet wrench 22, be used for the remainder of the installation. Detachment of the handle 18 also indicates to an installer that bone tissue density is sufficient to support both initial and long-term stabilization of a prosthesis. If the handle 18 never breaks off during installation, the installer knows that bone tissue 14 density is insufficient to properly support a prosthesis.

The handle 18 extends from an aft end 24 of the abutment 16 from a weakened area 26 that defines an interface between the handle 18 and the abutment 16. This weakened area 26 is configured to break under a pre-determined torque load of approximately 30 Newton-centimeters (30 Ncm). The handle 18, abutment 16, and shaft 12 are integrally formed with one another as a single unitary piece. The weak area is a neck formed at the interface between the handle 18 and the abutment 16.

The handle 18 is a contra-angle post that can be engaged and rotated by a low speed contra-angle rotary driver 20. The contra-angle rotary driver 20 rotates the device 10 at a speed in the range of approximately 20–50 rpm.

Figure 2:
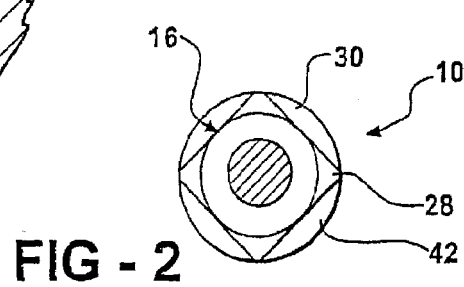
FIG. 2 is a cross-sectional front view of the device of FIG. 1.
Figure 3:
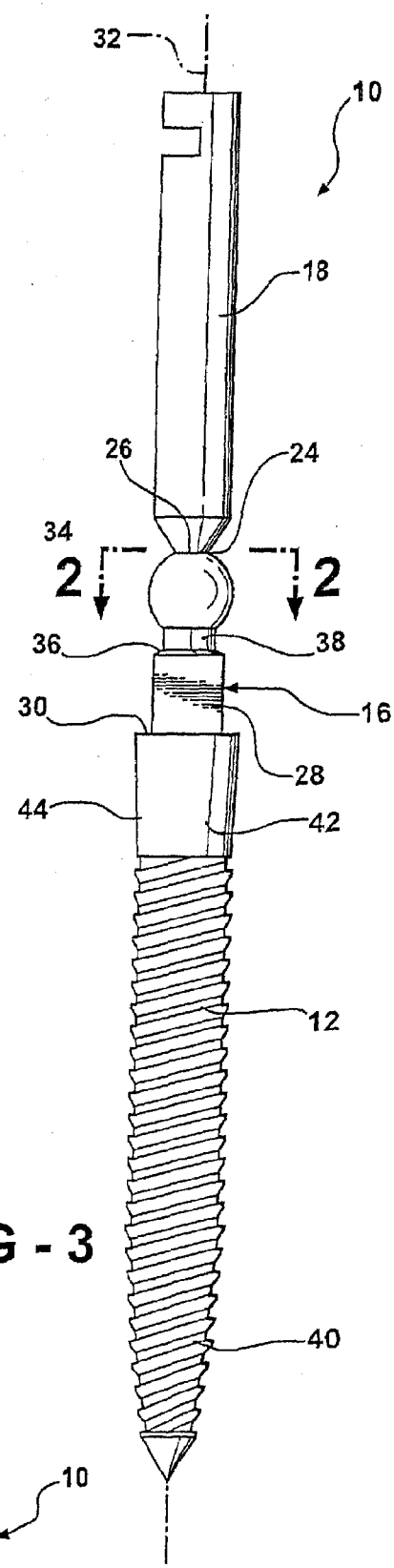
FIG. 3 is a cross-sectional view of the device of FIG. 1 taken along line 2—2 in FIG. 1.

The abutment 16 includes a nut 28 fixed to and axially extending from an aft end 30 of the threaded shaft 12. The nut 28 is shaped to be engaged and rotated by a tool adapted for that purpose. As best shown in FIG. 2, the nut 28 has a square cross section as measured perpendicular to a rotational axis 32 of the device 10. The nut 28 can be engaged and rotated by a ratchet wrench 22 or similar implement having a complimentary shaped engagement structure. In other embodiments, a nut and complimentary wrench of any other suitable configuration may be used instead of a square nut 28 and a wrench 22 with a square nut engagement box.

The abutment 16 also includes an O-ring abutment 34 fixed to and axially extending from an aft end 36 of the nut 28. The O-ring abutment 34 is an annular, generally spherical appendage known in the art as an "O-ball." The O-ring abutment 34 is designed to engage an O-ring disposed within a prosthesis according to any one of a number of different methods known in the art. The O-ring abutment 34 has a neck portion 38 where the O-ring abutment 34 merges with the aft end of the nut 28.

The threaded shaft 12 includes a tapered portion 40 shaped to wedge the shaft 12 into bone tissue 14 and instantly integrate with the bone tissue 14 upon installation. This increases initial stabilization and makes it possible to affix a permanent prosthesis to the O-ring abutment 34 immediately following installation.

The device 10 includes a collar 42 extending radially outward from around the aft end of the threaded shaft 12. The collar 42 is shaped to arrest threaded insertion of the device 10 at its proper depth. The shape of the collar 42 includes a frusto-conical surface 44 tapering radially outward and back from the threaded portion 12 of the shaft 12 to a point adjacent the aft end 30 of the shaft 12. Unlike the shaft 12, which has a relatively rough surface for bone integration, the collar is polished to promote adjacent soft tissue growth. The device 10 comprises a titanium alloy.

Figure 4:
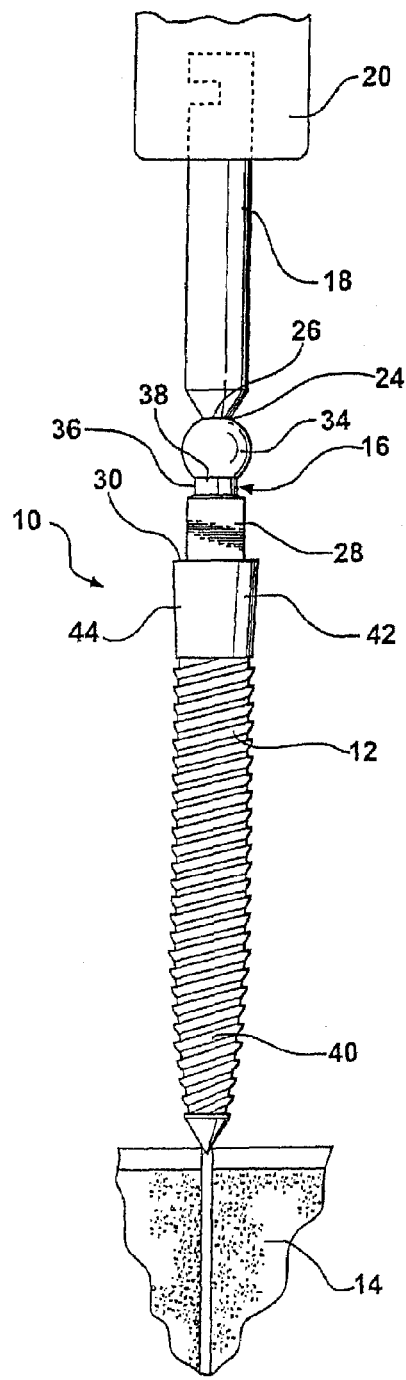
FIG. 4 is a front view of the prosthesis mounting device of FIG. 1 with a handle portion of the device connected to a rotary driver and a forward end of a threaded shaft portion of the device engaged in a small pilot hole formed in bone tissue.

In practice, a device 10 constructed according to the first embodiment of the invention can be secured in bone tissue 14 by first transporting the device 10 in a sterile condition within a sterile package. When the time comes to install the device 10, the package is opened and a rotary driver 20 is connected to the handle 18. The rotary driver 20 is then used to withdraw the device 10 from the package and to transport the device 10 to the surgical site. The mounting device 10 is then screwed into bone tissue 14 by first engaging the threaded shaft 12 with a pilot hole formed into the bone tissue 14 through the soft tissue 14 covering the jaw bone as shown in FIG. 4. The rotary driver 20 is then operated to rotate the device 10 until the handle 18 either breaks off or the device 10 is fully seated to a pre-determined depth.

Figure 5:
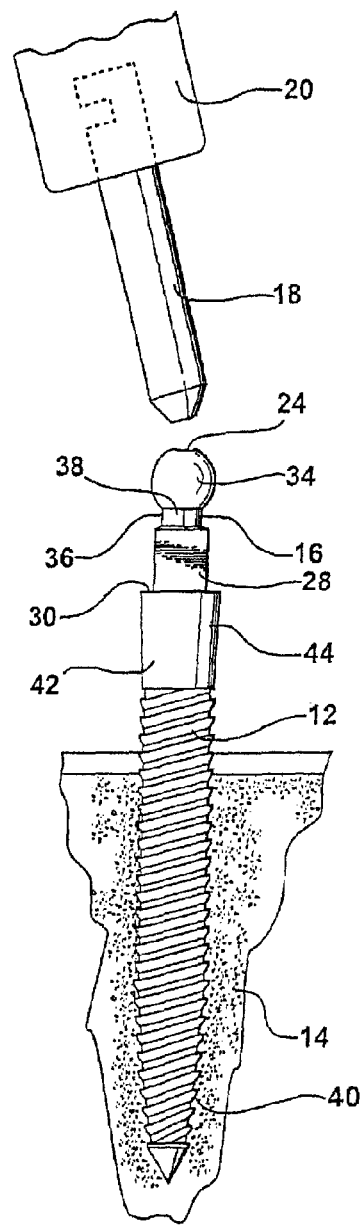
FIG. 5 is a front view of the prosthesis mounting device of FIG. 4 with the handle portion of the device broken off and the threaded shaft portion of the device partially screwed into the bone tissue.
Figure 6:
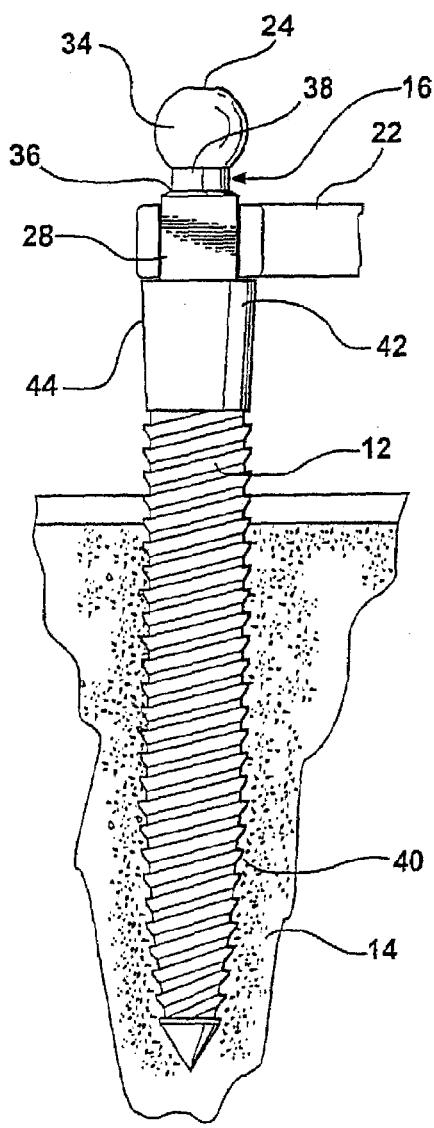
FIG. 6 is a front view of the prosthesis mounting device of FIGS. 4 and 5 with the handle portion removed and a ratchet wrench engaging a nut portion of an abutment of the device.
Figure 7:
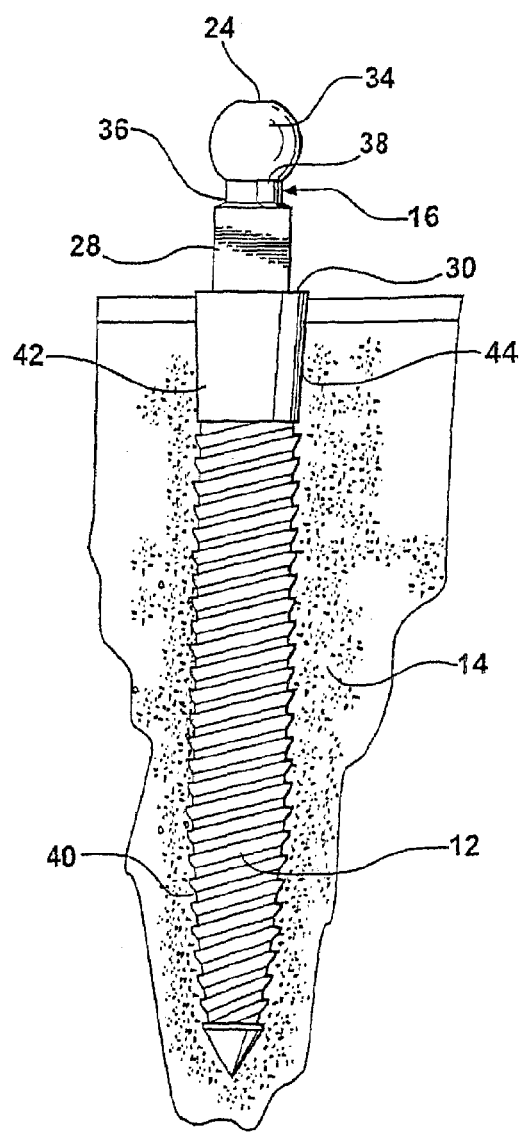
FIG. 7 is a front view of the prosthesis mounting device of FIGS. 4–6 shown after having been screwed into the bone tissue to a full desired depth.
Figure 11:
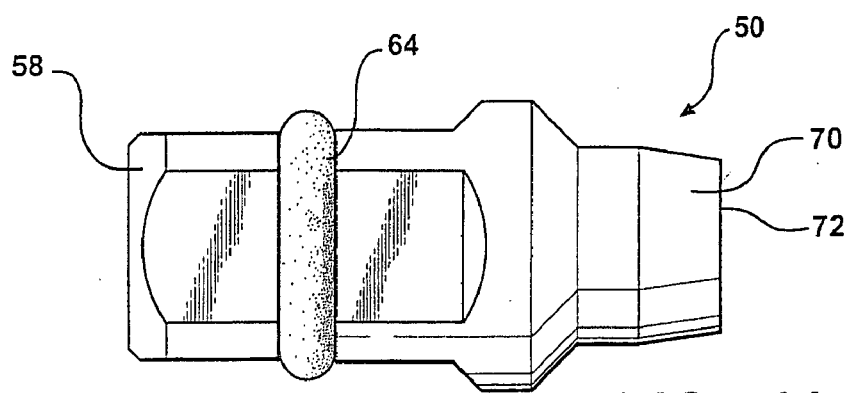
FIG. 11 is a front view of the driver adapter of FIG. 9.
Figure 12:
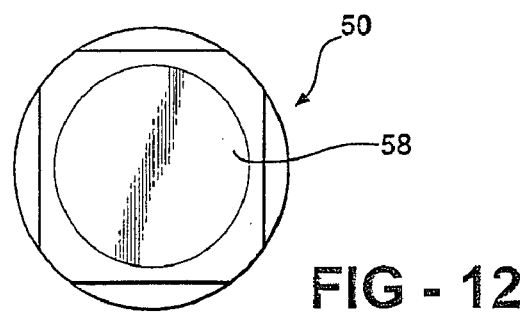
FIG. 12 is an end view of the driver adapter of FIG. 11.

If bone density is sufficient to properly support the device 10 and an attached prosthesis, the handle 18 breaks off before the device 10 reaches its full pre-determined depth as shown in FIG. 5. The mounting device 10 is then screwed to its full desired depth in the bone tissue 14 as shown in FIG. 7. This is accomplished by engaging and rotating the prosthetic abutment 16 with a manual ratchet wrench 22 or similar implement as shown in FIG. 6.

If the handle 18 does not break off before the device 10 reaches its desired depth, the mounting device 10 is removed from the bone tissue 14 and an alternative prosthetic mounting method and/or device 10 more adaptable to supporting a prosthesis on soft bone tissue 14 is selected.

In addition to its breakaway feature, the installation handle 18 of the device 10 provides a hands-free delivery system. It allows a device 10 to be retrieved from a sterile container and transported to a surgical site without contaminating the portion of the shaft 12 to be implanted in bone tissue 14. The handle 18 also serves to transmit torque from a rotary driver 20 to the device 10 for threading the device 10 into bone tissue 14 without damaging the abutment 16. Abutment 16 damage can comprise secure attachment of a prosthesis to the device 10.

The device 10 is a "mini" dental implant dimensioned to self-tap into bone tissue starting at a small, approximately ¼" deep starter hole. The shaft portion 12 of the device 10 is approx. 1.8 mm in diameter. However, in other embodiments, the shaft may be up to approximately 2 mm in diameter depending on the visco-elastic properties of the bone.

The second prosthesis mounting device embodiment 10' is essentially identical to the first, embodiment 10 except that the second embodiment includes no installation handle. Instead, as shown in FIG. 8, an O-ball 34' defines an upper end of the device 10'.

Figure 13:
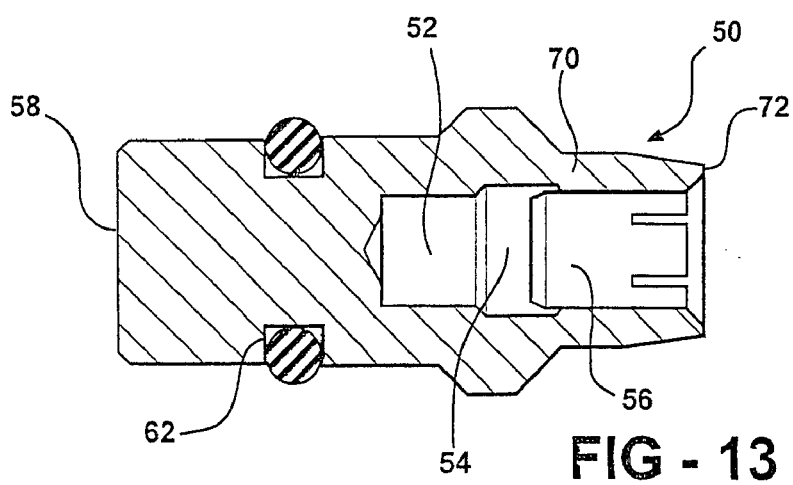
FIG. 13 is a cross-sectional front view of the driver adapter of FIG. 9.
Figure 14:
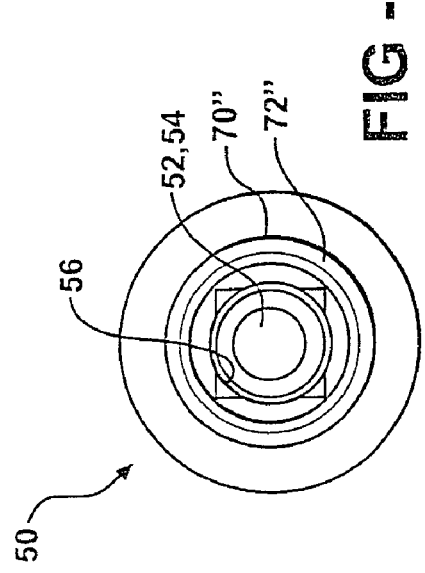
FIG. 14 is an end view of the driver adapter of FIG. 9 showing an end opposite the end shown in FIG. 12.

Because the second mounting device embodiment 10' includes no integral installation handle, the invention also comprises a driver adapter 50 that receives the O-ball 34' and the square nut 28' into a complementary-shaped recess that's best shown at 52 in FIG. 13. An inner chamber 54 of the recess 52 is shaped to releasably retain the O-ball 34' in snap-fit fashion. An outer section 56 of the recess 52 is shaped to rotatably engage the nut when the O-ball 34' is fully received into the inner chamber 54.

Figure 15:
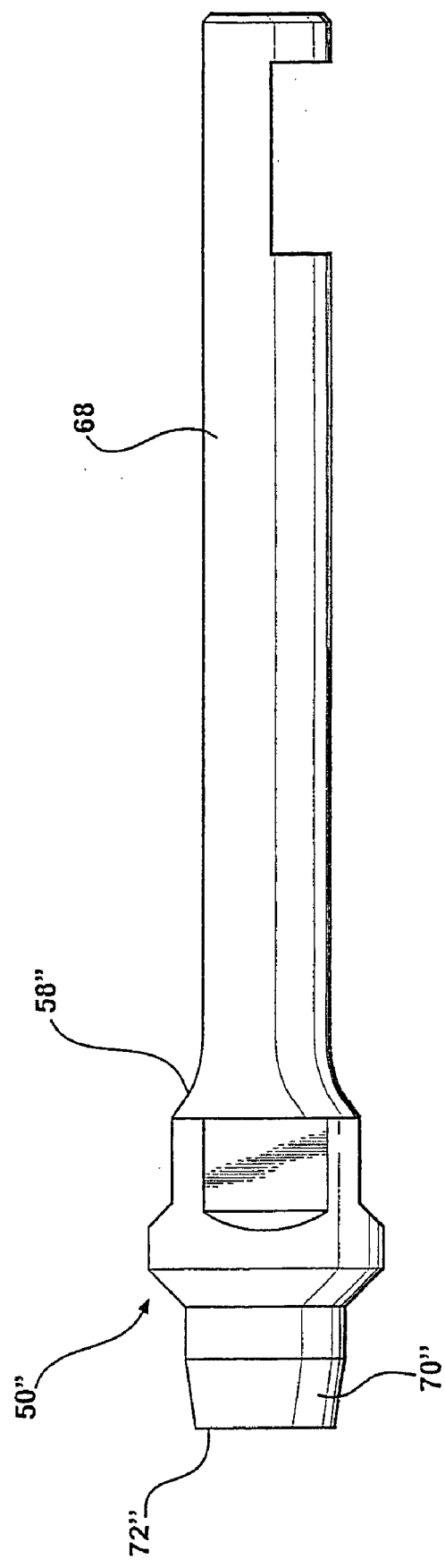
FIG. 15 is a front view of an alternative driver adapter embodiment.

An upper end 58 of the driver adapter 50 has a generally square cross-section shaped to be received into and rotatably engaged by a socket portion 60 a standard ratchet wrench 22' as shown in FIG. 10. A peripheral trench 62 is formed around the upper end 58 of the driver adapter 50 and a rubber O-ring 64 is received into the trench 62 as shown in FIGS. 9, 10, 12, and 13. The O-ring 64 provides an interference fit between the upper end 58 of the driver adapter 50 and an inner surface 66 of a ratchet wrench 22' that prevents the driver adapter 50 from falling out of a ratchet wrench 22' during transport to an osteotomy site. In other embodiments, such as the one shown in FIG. 15, a contra-angle drill adapter shaft 68 may be attached to or integrally formed with the driver adapter 50" and extend axially from the upper end 58" of the driver adapter 50". Such a contra-angle shaft would allow an installer to use a contra-angle drill to install the device. In either case, an installer can engage the mounting device 10', using either a ratchet wrench 22' or a contra-angle drill, and remove the device 10' from its sterile packaging without contaminating the device. The installer can then transport the mounting device 10' to an osteotomy site and install the device without ever touching or otherwise contaminating it.

Figure 16:
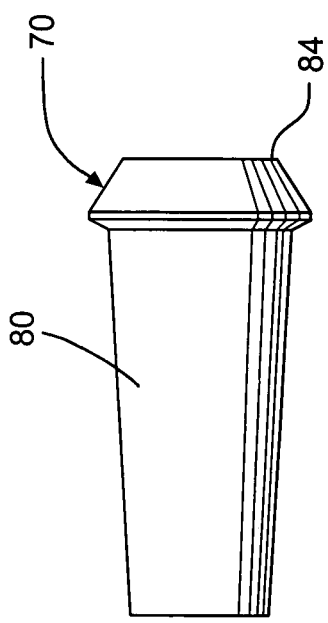
FIG. 16 is a side view of a prosthesis mounting device constructed according to the invention.
Figure 17:
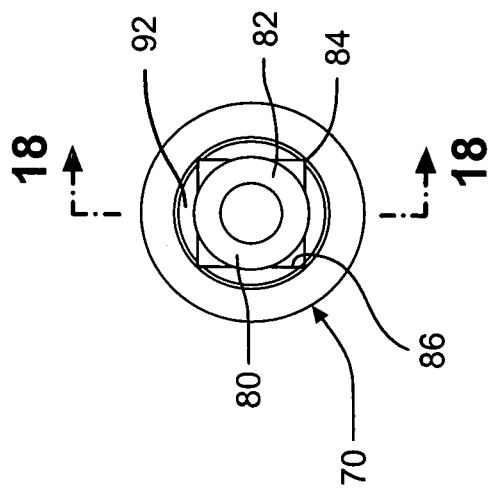
FIG. 17 is a right end view of the prosthesis mounting device of FIG. 16.
Figure 18:
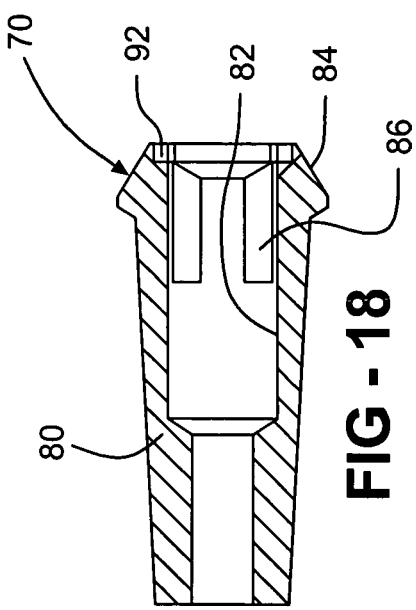
FIG. 18 is a cross-sectional side view of the prosthesis mounting device of FIGS. 16 and 17 and is taken along line 18—18 of FIG. 17.

A third embodiment of a prosthesis mounting device for securing a prosthesis on an implant supported in bone tissue is generally indicated at 70 in FIGS. 16–18. A prosthesis mounting assembly 72 for securing a prosthesis on an implant supported in bone tissue is generally shown at 72 in FIG. 19 and includes the prosthesis mounting device 70 of FIGS. 16–18 and a miniature dental implant 74 having an O-ring receiver abutment 76 attached to and axially extending from an aft end of a threaded shaft 78 or bone screw.

The prosthesis mounting device 70 includes a titanium appendage or preppable abutment 80 that's shaped to be carried by a dental implant 74 or "tooth post". The preppable abutment 80 is milled, or "prepped", as a tooth would be prepped, into a generally triangular prism-like shape, or any other shape suitable to accept and carry a dental prosthetic such as a crown or a bridge. The device 70 also includes a recess 82 or axial channel that extends axially upwardly from an axial bottom end 84 of the preppable abutment 80. As is best shown in FIG. 19, the recess 82 is shaped to fit over an O-ball abutment or O-ring receiver abutment 76 of a miniature dental implant 74.

The recess 82 includes an axially lower portion 86 configured to engage a multi-faceted nut 88 of a dental implant 74 to limit rotation of a prosthetic relative to the preppable abutment 80. The axially lower portion 86 of the recess 82 is shaped to complement the shape of the multi-faceted nut 88 of the implant 74 to provide superior anti-rotation characteristics—as is particularly important in single-toothed prosthetic applications.

The recess 82 is shaped to fit closely over the O-ball receiver abutment 76 and the multifaceted nut 88 of the implant 74 to minimize micro-movement between the preppable abutment 80 and the implant 74. In the present embodiment, the multi-faceted nut 88 has a square cross-section as measured perpendicular to a rotational axis of the device 70 and the recess 82 of the preppable abutment 80 has a generally square cross-section shaped to complement and receive the nut 88. In other embodiments, the nut 88 and recess 82 may have complementary cross-sectional shapes that are other than square.

Figure 19:
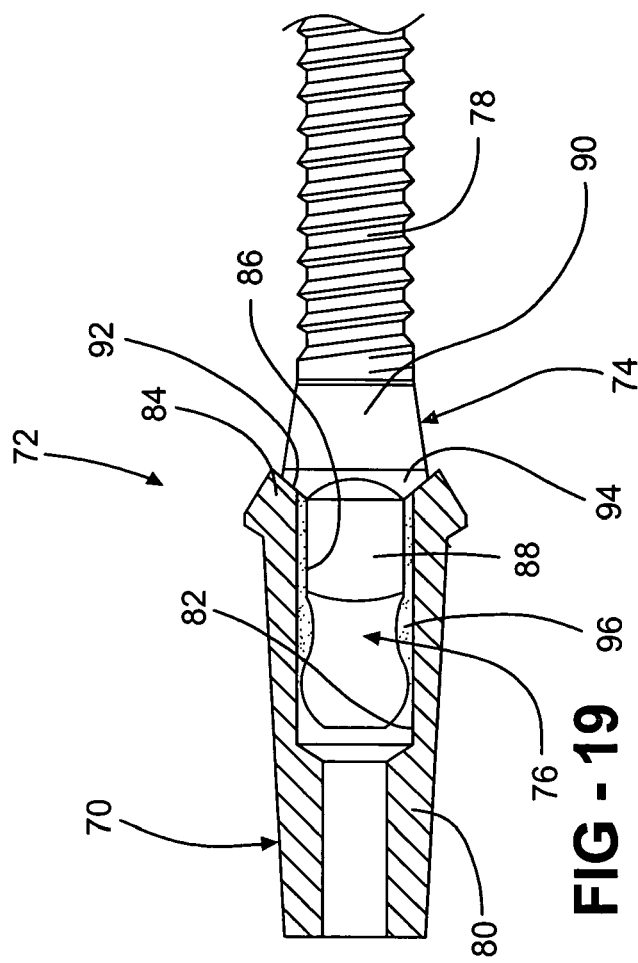
FIG. 19 is a partial cross-sectional side view of a prosthesis mounting assembly constructed according to the invention and showing the O-ring receiver abutment of an implant of the assembly received within the preppable abutment of FIGS. 16–18.

The recess 82 has an opening 92 shaped to receive a collar 90 that extends radially outward from around an aft end of the threaded shaft 78 of the implant 74 as best shown in FIG. 19. In the present embodiment, the opening 92 to the recess 82 has a frustoconical shape complimenting the shape of an upper, generally annular ramped surface 94 of the collar 90. This further secures the prosthesis mounting device 70 or preppable abutment 80 against micro-movement. As is also shown in FIG. 19, a layer of resin cement 96 bonds the O-ring receiver abutment 76 to the preppable abutment 80.

In practice, a prosthesis can be secured on an implant 74 supported in bone tissue by first installing one or more implants 74 in a patient's jaw bone within the patient's oral cavity, each implant 74 including an O-ring receiver abutment 76. The procedure for installing such an implant 74 is well-known in the art and is described in detail above. A preppable abutment 80 constructed according to the invention is then removably supported on each implant 74 by providing each preppable abutment 80 over a corresponding one of the O-ring receiver abutments 76 in respective positions for respective axially lower ends of the preppable abutments 80 engage respective upper surfaces 94 of the implant collars 90. The preppable abutments 80 are then prepped by milling each preppable abutment 80 as required to accommodate one or more dental prosthetics such as a bridge or respective prosthetic teeth. Each prepped abutment is milled to achieve parallelism, i.e., a parallel relationship between the surfaces of each preppable abutment 80, to provide a tighter fit over the O-ring receiver abutments 76 and a parallel relationship between the surfaces of adjacent preppable abutments 80 to allow a bridge to be slid over all the preppable abutments 80 along a single line of motion. The achievement of parallelism between abutments is important when multiple implants 74 and preppable abutments 80 are used. This is because, typically, every implant 74 is angled a little bit differently after it has been installed in bone tissue. The preppable abutments 80 are therefore machined in such a way as to correct for such differences in alignment or orientation.

One or more dental prosthetics are then formed to be supported on each of the preppable abutments 80. This is done by pressing an impression tray over each preppable abutment 80, and picking up each preppable abutment 80 in the impression tray such that the preppable abutments 80 serve as their own impression copings. An O-ball abutment analog is then inserted into each preppable abutment 80 carried in the impression tray. The O-ball abutment analogs are devices having the same size and shape as the O-ball abutments of the mini implants 74. Liquid casting material is then provided in the impression tray and allowed to harden into a model of the patient's teeth and gums in the vicinity of and surrounding the preppable abutments 80 and implants 74. The model is then removed from the impression tray and the preppable abutments 80 are also removed from the impression tray. The overall abutment analogs are then removed from each of the preppable abutments 80 and the preppable abutments 80 are then supported on the implants 74. The preppable abutments 80 are cemented onto the implants 74 with resin cement and then a metal reinforced bridge is cemented onto the preppable abutments 80.

This description is intended to illustrate certain embodiments of the invention rather than to limit the invention. Therefore, it uses descriptive rather than limiting words. Obviously, it's possible to modify this invention from what the description teaches. Within the scope of the claims, one may practice the invention other than as described.

What is claimed is:

1. A prosthesis mounting assembly for securing a prosthesis on an implant supported in bone tissue, the prosthesis mounting assembly comprising:
    an implant including a threaded shaft configured to be screwed into bone tissue, an O-ball abutment, and a multi-faceted integral nut attached to and axially extending from an aft end of the shaft;
    a metallic appendage that's configured to be carried by the dental implant, and to be milled into a shape suitable to accept a dental prosthetic; and
    a recess that extends axially upwardly into the appendage from an axial bottom end of the appendage, the recess including an inner wall having a cylindrical portion shaped to engage and fit closely over the O-ball abutment of the dental implant and a multi-faceted portion shaped to engage and fit closely around the integral nut of the implant, forming an annular cement retention cavity between the recess wall and an undercut portion of the implant that is defined by a lower hemisphere of the O-ball abutment of the implant.

2. A prosthesis mounting assembly as defined in claim 1 in which the recess includes an axially lower portion configured to engage a multi-faceted integral nut of the dental implant.

3. A prosthesis mounting assembly as defined in claim 2 in which the axially lower portion of the recess is shaped to complement the shape of the multi-faceted integral nut of the implant.

4. A prosthesis mounting assembly as defined in claim 1 in which:
    the implant abutment is an O-ring receiver abutment; and
    the metallic appendage is a preppable abutment that fits over and engages the O-ring receiver abutment of the implant.

5. A prosthesis mounting assembly as defined in claim 4 in which the nut of the implant is fixed to and extends axially from the aft end of the threaded shaft and is configured to be engaged and rotated by a tool adapted for that purpose.

6. A prosthesis mounting assembly as defined in claim 5 in which:
    the nut has a square cross section as measured perpendicular to a rotational axis of the implant; and
    the preppable abutment includes an axial channel, at least a portion of the channel having a generally square cross section shaped to complement and receive the nut.

7. A prosthesis mounting assembly as defined in claim 5 in which the O-ring receiver abutment of the implant includes a generally spherical appendage fixed to and axially extending from an aft end of the nut, the generally spherical appendage being configured to engage an O-ring carried within a prosthesis or a preppable abutment.

8. A prosthesis mounting assembly as defined in claim 7 in which the O-ring receiver abutment of the implant has a neck portion where the O-ring receiver abutment merges with the aft end of the nut.

9. A prosthesis mounting assembly as defined in claim 4 in which the threaded shaft is configured to self-tap into a small pilot hole formed in bone tissue.

10. A prosthesis mounting assembly as defined in claim 4 in which the implant includes a collar that extends radially outward from around the aft end of the threaded shaft and includes an upper annular surface positioned to engage and support an axial lower end of the preppable abutment.

11. A prosthesis mounting assembly as defined in claim 10 in which the collar includes a frusto-conical outer surface tapering radially outward from the threaded portion of the shaft to a point adjacent the aft end of the shaft.

12. A method for securing a prosthesis on an implant supported in bone tissue, the method including:
    installing one or more implants in a patient's jaw bone, each implant including an O-ring receiver abutment;
    removably supporting a preppable abutment on the or each implant;
    prepping the or each preppable abutment by milling each preppable abutment as required to accommodate one or more dental prosthetics;
    forming one or more dental prosthetics to be supported on the or each preppable abutment; and
    supporting the or each preppable abutment on the or each implant.

13. The method of claim 12 in which the step of removably supporting a preppable abutment on the or each implant includes providing the preppable abutment over the O-ring receiver abutment in a position where an axially lower end of the preppable abutment engages an upper surface of a collar of the implant.

14. The method of claim 12 in which the step of prepping the or each preppable abutment includes milling each preppable abutment to achieve parallelism.

15. The method of claim 12 in which the step of forming one or more dental prosthetics to be supported on the or each preppable abutment includes:
   pressing an impression tray over the or each preppable abutment;
   picking up the or each preppable abutment in the impression tray;
   inserting an O-ball abutment analog into the or each preppable abutment carried in the impression tray;
   providing liquid casting material in the impression tray and allowing to harden into a model of a patient's teeth and gums in the vicinity of and surrounding the or each preppable abutment and implant;
   removing the model from the impression tray;
   removing the or each preppable abutment from the impression tray; and
   removing the or each O-ball abutment analog from the or each preppable abutment.

16. The method of claim 12 in which the step of supporting the or each preppable abutment on the or each implant includes cementing the or each preppable abutment over the or each implant.

17. The method of claim 12 in which the step of supporting the or each preppable abutment on the or each implant includes cementing a metal reinforced bridge onto the or each preppable abutment.

* * * * *

UNITED STATES PATENT AND TRADEMARK OFFICE
CERTIFICATE OF CORRECTION

| | |
|---|---|
| PATENT NO. | : 7,217,130 B2 |
| APPLICATION NO. | : 10/453309 |
| DATED | : May 15, 2007 |
| INVENTOR(S) | : Thierry Giorno |

Page 1 of 1

It is certified that error appears in the above-identified patent and that said Letters Patent is hereby corrected as shown below:

Column 7, line 27, "comprise" should be --compromise--

Column 7, line 37, delete [[,]] after "first"

Signed and Sealed this

Twenty-second Day of July, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,217,130 B2 | Page 1 of 1 |
| APPLICATION NO. | : 10/453309 | |
| DATED | : May 15, 2007 | |
| INVENTOR(S) | : Thierry Giorno | |

It is certified that error appears in the above-identified patent and that said Letters Patent is hereby corrected as shown below:

The text beginning with "The driver adapter recess 52..." at column 5, line 24 and extending to "...as shown in FIG. 10" at column 5, line 55, should be deleted and inserted before the paragraph beginning at column 9, line 39.

Signed and Sealed this

Thirteenth Day of January, 2009

JON W. DUDAS
*Director of the United States Patent and Trademark Office*

UNITED STATES PATENT AND TRADEMARK OFFICE
CERTIFICATE OF CORRECTION

PATENT NO.         : 7,217,130 B2
APPLICATION NO.    : 10/453309
DATED              : May 15, 2007
INVENTOR(S)        : Thierry Giorno Page 1 of 1

It is certified that error appears in the above-identified patent and that said Letters Patent is hereby corrected as shown below:

The text beginning with "The driver adapter recess 52…" at column 5, line 24 and extending to "…as shown in FIG. 10" at column 5, line 55, should be deleted and inserted before the paragraph beginning at column 9, line 39.

Signed and Sealed this

Seventeenth Day of February, 2009

JOHN DOLL
*Acting Director of the United States Patent and Trademark Office*

UNITED STATES PATENT AND TRADEMARK OFFICE
CERTIFICATE OF CORRECTION

PATENT NO.         : 7,217,130 B2                                           Page 1 of 1
APPLICATION NO. : 10/453309
DATED              : May 15, 2007
INVENTOR(S)        : Thierry Giorno It is certified that error appears in the above-identified patent and that said Letters Patent is hereby corrected as shown below:

This certificate vacates the Certificate of Correction issued February 17, 2009. The certificate is a duplicate of the Certificate of Correction issued January 13, 2009. All requested changes were included in the Certificate of Correction issued January 13, 2009.

Signed and Sealed this

Seventeenth Day of March, 2009

JOHN DOLL
*Acting Director of the United States Patent and Trademark Office*